(12) United States Patent
Fine et al.

(10) Patent No.: US 6,423,692 B2
(45) Date of Patent: *Jul. 23, 2002

(54) METHOD OF ENHANCING THE EFFECTIVENESS OF DCK PHOSPHORYLATED MOLECULES

(75) Inventors: Howard A. Fine, Boston; Donald Kufe, Wellesley, both of MA (US); Yoshinobu Manome, Kawasaki (JP)

(73) Assignee: Dana-Farber Cancer Institute, Inc., Boston, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/065,933

(22) Filed: Apr. 24, 1998

Related U.S. Application Data
(60) Provisional application No. 60/044,314, filed on Apr. 24, 1997.

(51) Int. Cl.$^7$ .......................... A01N 63/00; A61N 48/00; C12P 21/06; C12N 15/00; C12N 15/63
(52) U.S. Cl. ................. 514/44; 435/69.1; 435/320.1; 435/325; 435/455; 514/44; 514/45; 514/49; 424/93.2
(58) Field of Search ...................... 514/44, 45, 49, 514/69.1; 435/320.1, 325, 455; 424/93.1, 93.2; 536/23.1, 23.5

(56) References Cited

PUBLICATIONS

Hapke et al, Proc. Annu. Meet. Am. Assoc. Cancer Res 37:A2910, 1996.*
Friedmann, Gene Therapy 1:217–218, 1994.*
Mulligan, Science 260:925–932, 1993.*
Blu et al N Engl J Med. 333(18):1204–7 1995.*
Wen et al, Neurology, 46(2): S5, pp44, 1996.*
Vile et al, Gene Therapy, 1:88–98, 1994.*
Anderson WF, Nature 392:25–30, 1998.*
Verma et al Nature 389:239–242, 1997.*
Touchette, Nat. Med. 2(1) 7–8, 1996.*
Fahraeus et al J. Pathol. 187:138–146, 1999.*
Kay et al, PNAS 94:12744–12746, 1997.*
Blu et al N Engl J Med. 333(18):1204–7 1995.*
J. Durham, et al., ("Deoxycytidine Kinase", The Journal of Biological Chemistry, vol. 245, No. 9, pp. 2276–2284, 1970).
Aster Habteyesus, et al., ("Deoxynucleoside Phosphorylating Enzymes In Monkey and Human Tissues Show Great Similarities, While Mouse Deoxycytidine Kinase Has a Different Substrate Specificity", Biochemical Pharmacology, vol. 42, No. 9., pp. 1829–1836, 1991).

Dah Hsi Wang Ho, ("Distribution of Kinase and Eaminase of 1–B–D–Arabinofuranosylcytosine in Tissues of Man and Mouse", Cancer Research, 2816–2820, Nov. 1973).

J. Durham, et al., ("Deoxycytidine Kinase", Mol. Pharmacol 5, 358–375, 1969).

Frederick L. Moolten, ("Tumor Chemosensitivity Conferred by Inserted Herpes Thymidine Kinase Genes: Paradigm for a Prospective Cancer Control Strategy", Cancer Research 46, 5276–5281, Oct. 1986).

Dennis A. Carson, et. al., ("Specific Toxicity of 2–Chlorodeoxyadenosine Toward Resting and Ptoloferating Human Lymphocytes", Blood, vol. 62, No. 4, Oct. 1983, pp. 737–743).

Dennis A. Carson, et al., ("Deoxycytidine Kinase–Mediated Toxicity of Deoxyadenosine Analogs Toward Malignant Human Lymphoblasts In Vitro and Toward Murine L1210 Leukemia In Vivo", Proc. Natl. Acad. Sci, USA, vol. 77, No. 11, pp. 6865–6869, Nov. 3, 1980, Medical Sciences).

Vernon Verhoef, et al., ("Identification of the Mechanism of Activation of 9–B–D–Arabinofuranosyladenine in Human Lymphoid Cells using Mutants Deficient In Nucleoside Kinases", Cancer Research 41, 4478–4483, Nov. 1981).

Wen–Cheng Tseng, et al., ("In Vitro Biological Activity of 9–B–D–Arabinofuranosyl–2–Fluroadenine and the Biochemical Actions of Its Triphosphate on DNA Polymerases and Ribonucleotide Reductase from HeLa Cells", Molecular Pharmcology, 21:474–477).

Jay C. Sarup, et al., ("Regulation of Purine Deoxynucleoside Phosphorylation By Deoxycytidine Kinase From Human Leukemic Blast Cells", Biochemical Pharmacology, vol. 38, No. 16, pp. 2601–2607, 1989, printed in Great Britain).

Nabanita S. Datta, et al. ("Human T–Lymphoblast Deoxycytidine Kinase: Purification and Properties", Biochemistry, 1989, 28, 114–123).

Staffan Ericksson, et al. ("Comparison of The Substrate Specificities of Human Thymidine Kinase 1 and 2 and Deoxycytidine Kinase Toward Antiviral and Cytostatic Nucleoside Analogs", Biochemical and Biophysical Research Communications).

(List continued on next page.)

*Primary Examiner*—Scott D. Priebe
*Assistant Examiner*—Sumesh Kaushal
(74) *Attorney, Agent, or Firm*—Nixon Peabody LLP

(57) ABSTRACT

A method of increasing the effectiveness of molecules that can be phosphorylated by dCK is described. This method involves transducing cells with the gene for deoxycytidine kinase which can chemosensitize the cell to molecules that are phosphorylated by dCK.

18 Claims, 7 Drawing Sheets

OTHER PUBLICATIONS

E. Boven, et al., ("The Influence Of The Schedule And The Dose Of Gemcitabine On The Anti–tumour Efficacy In Experimental Human Cancer", Correspondence: E. Boven, received Aug. 27, 1992; and in revised form Mar. 1, 1993).

Boudewijn, J.M. Braakhuis, ("Preclinical in Vivo Activity of 2',2'–Difluorodeoxycytidine (Gemcitabine) Against Human Head and Neck Cancer", Cancer Research, 51, 211–214, Jan. 1, 1991).

Larry W. Hertel et al., (Evaluation of The Antitumor Activity of Gemcitabine (2', 2'–Difluoro–2'–Deoxycytidine).

Volker Heinemann, et al., ("Comparison of The Cellular Pharmacokinetics and Toxicity of 2',2'–Difluorodeoxycytidine and 1–B–D–Arabinofuranosylcytosinel", Cancer Research 48, 4042–4031, Jul. 15, 1988).

D.J. Richel, et al., ("Comparison of the Antileukaemic Activity of 5 Aza–2–Deoxycytidine And Arabinofuranosyl–Cytosine In Rats With Myecolyctic Leukaemia", Correspondence: D.J. Richel, Received Mar. 27, 1998; and in revised form, Jul. 25, 1988).

Donald Kufe, et al., ("Relationships Among Ara–CTP Pools, Formation of (ARA–C) DNA, and Cytoxicity of Human Leukemic Cells", Blood, vol. 64, No. 1 (Jul.), 1984: pp. 54–58).

Donald W. Kufe ("Correlation of Cytotoxicity With Incoporation of Ara–C Into DNA", The Journal of Biological Chemistry vol. 255, No. 19, Issue of Oct., pp 8997–9000, 1980).

F.L. Graham ("Studies in Mouse L–cells on the Incorporation of 1–B–D–Arabinofuranosylcytosine into DNA and on Inhibition of DNA Polymerase by 1–B–D–Arabinofuranosylcytosine 5'–Triphosphate1", Cancer Research 30, 2636–2644, Nov. 1970).

Steven Grant ("Biochemical Modulation of Cytosine Arabinoside", *Pharma: Ther. vol. 48,* pp. 29–4, 1990).

E. Cadman et al., ("Combination Therapy for Diffuse Histiocytic Lymphoma That Includes Antimetabolites1", *Cancer Treatment Reports*, vol. 61, No. 6, Sep. 1977).

Rose Ruth Ellison et al., ("Arabinosyl Cytosine: A Useful Agent in the Treatment of Acute Leukemia in Adults", *Blood*, vol. 32, No. 4 Oct. 1968).

Yoshinobu Manome et al., ("Viral Vector Transduction of the Human Deoxycytidine Kinase cDNA Sensitizes Glioma Cells To The Cytotoxic Effects of Cytosine Arabinoside In Vitro and In Vivo", H. Fine, Feb. 19, 1996).

Veronique W.T. Ruiz van Haperen et al., ("New Targets For Pyrimidine Antimetabolites For The Treatment of Solid Tumours", Planning World of Science).

* cited by examiner

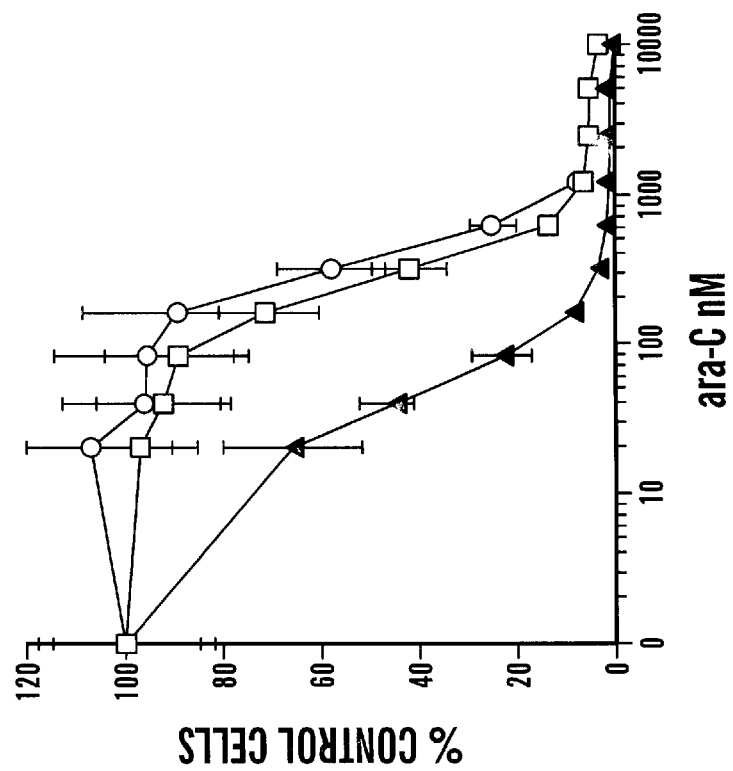
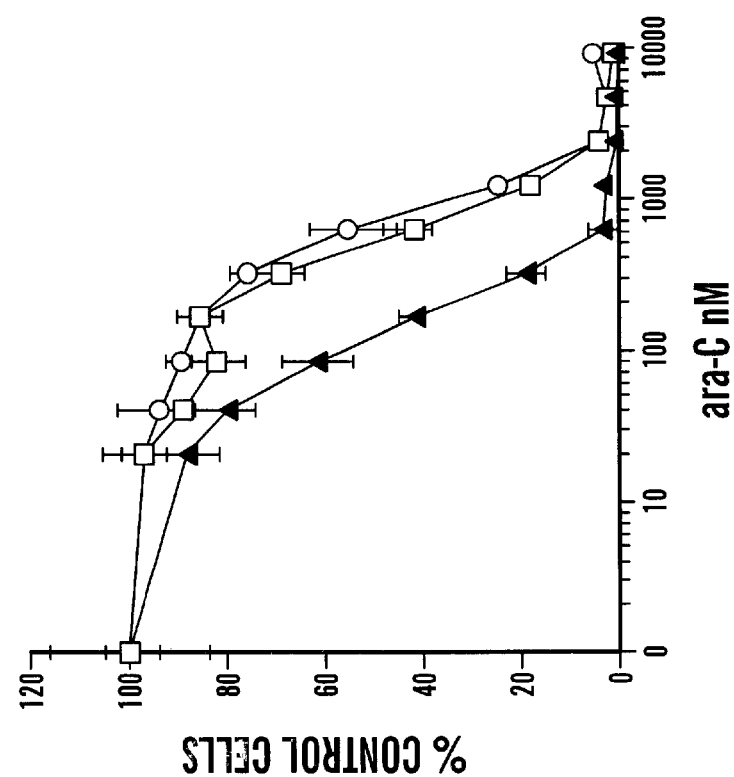

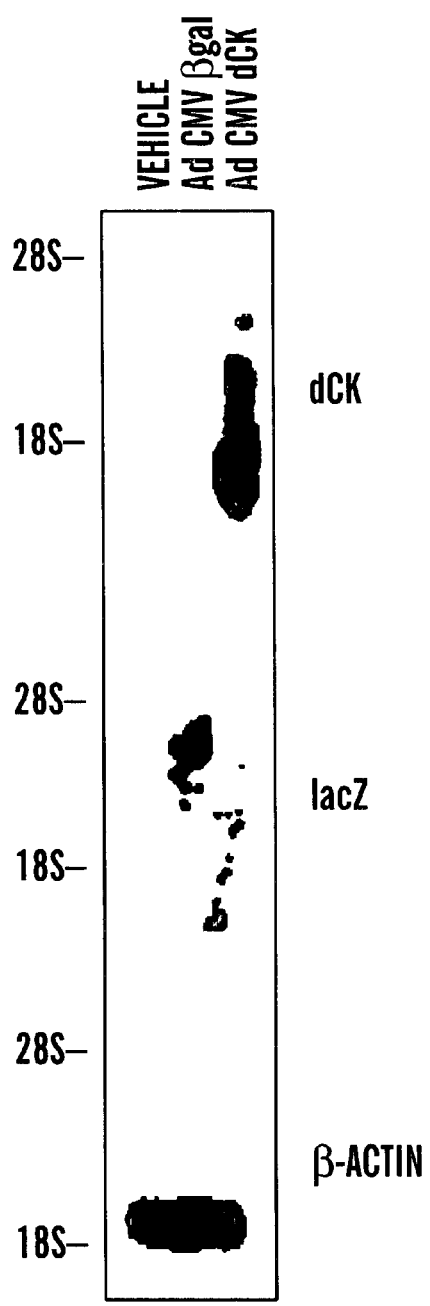
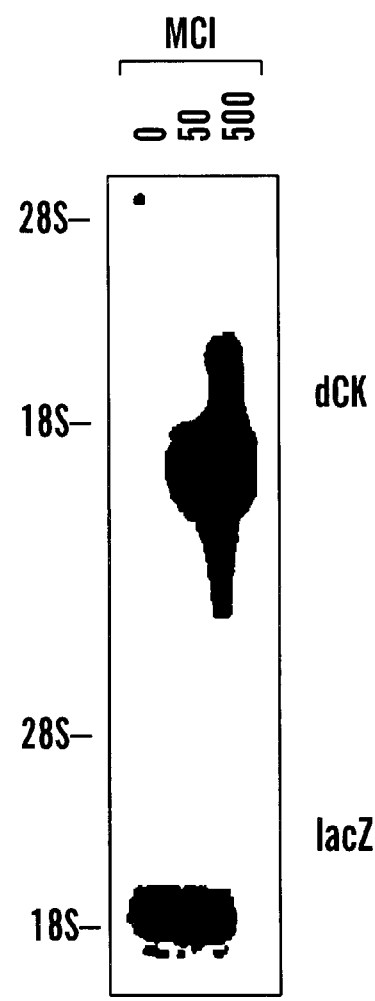
*FIG. 5A*
*FIG. 5B*

METHOD OF ENHANCING THE EFFECTIVENESS OF DCK PHOSPHORYLATED MOLECULES

This application claims the benefit of U.S. Provisional Application No. 60/044,314 filed Apr. 24, 1997.

BACKGROUND

The present invention is directed to a method of increasing the effectiveness of molecules that are phosphorylated in their active state. This is accomplished by transducing cells with the gene for deoxycytidine kinase resulting in the chemosensitization of such cells which are targets for those molecules. Preferably, the target cells are virally infected cells and/or tumor cells. Preferred tumor cells are solid tumor cells such as brain tumors.

Deoxycytidine kinase (dCK) is an enzyme that catalyses the phosphorylation of a variety of pyrimidine and purine deoxynucleosides to their corresponding nucleotide [Ruiz van Haperen and Peters, *Urine and Pyrimidine Metabolism* 15: 104–112 (1994)]

A number of the above-mentioned deoxynucleoside molecules when phosphorylated by dCK are "activated" and display an antineoplastic and/or antiviral activity. For example Ara-C (1-β-D-arabinofuranosyl-cytosine also referred to as cytarabine) is presently one of the most effective agents in the treatment of acute myeloid leukemia [Ellison, R. R., et al. *Blood* 32:407–523 (1968); Cadman, E. et al., *Cancer Treat. Rep.* 61:1109–1116 (1977); Balwell, B., et al., *Leukemia* 2: 253–60 (1988); Momparler, R. L., et al. Drug Resistance to Cytosine Arabinoside, in: Kessel D., Ed, *Resistance to Antineoplastic Drugs*, Boca Raton; CRC Press, 353–67 (1989); Grant, S., *Pharmacol. Ther.* 48:29–44 (1990)]. Ara-C is incorporated into replicating DNA and terminates DNA chain elongation [Graham, F. L., et al., *Cancer Res.* 30:2636–3644 (1970); Kufe, W. D., et al., *J. Biol. Chem.* 225:8997–9000 (1980); Kufe, D., et al., *Blood* 64:54–58 (1984)]. Unfortunately Ara-C has shown limited activity against most solid tumors including brain tumors. Aza-CdR (sometimes referred to as decitabine or 5-aza-2'-deoxycytidine) has shown considerable activity in treating both experimental leukemia and human acute myelogenous leukemia [Richei, D., et al., *Br. J. Cancer,* 58:730–3 (1988) Richei, D., et al., *Contrib. Oncology,* 37:20–9 (1989) Pinto, A., et al., *Leukemia Supp,.* 1:51–60 (1993)]. dFdC (2,2'-difluorodeoxycytidine or gemcitabine) [Heinemann, V., et al., *Cancer Res.* 48:4024–31 (1988)] has shown preclinical activity against a number of experimental tumors and human xenografts [Hertel, L. W., et al., *Cancer Res.* 50:4417–4422 (1990); Braakhuis, B. J. M., et al., *Cancer Res.,* 51:211–214 (1991); Boven E., et al., *Br. J. Cancer* 68:52–56 (1993)]. Other molecules include cladribine (2-chloro-2'-deoxyadenosine) [Erikson, S., et al., *Biochem. Biophys. Res. Commun.,* 176:586–592 (1991)], zalcitabine (2', 3'-dideoxycitidine) [Datta, N. S., et al., *Biochemistry* 28:114–123 (1989); Sarup, J. C., et al., *Biochem. Biophys. Res. Commun.,* 176:586–592 (199 1)] and fludarabine (9-β-D-arabinofuranosyl-2-fluoroadenine) [Tseng W., et al., *Mol. Pharmacol.* 21:474–477 (1982)].

The mode of activation of these molecules is similar. For example, fludarabine monophosphate is dephosphorylated extracellularly to fludarabine, which is then transported into the cell. Where dCK phosphorylates this molecule [Verhoef, V., et al. *Cancer Res.* 41:4478–4483 (1981)] into the monophosphate form which is then converted to the triphosphate derivative, which is a potent inhibitor of DNA polymerase and ribonucleotide reductase.

dCK phosphorylates cladribine into its active state [Carson, D. A., et al., *Proc. Natl. Acad. Sci. USA,* 77:6865–6869 (1980)], where it exhibits activity against a number of leukemia cell lines, but has not shown much activity against most non-lymphoid solid tumors [Carson, D. A., et al., *Blood* 62:737 (1983)]. However, it has been found to be active against the human ovarian carcinoma cell line A2780 [Ruiz van Haperen, V. W. T., et al., *Proc. Am. Assoc. Cancer Res.,* 34:307 (1993)].

It would be very valuable if the relative effectiveness of any of these molecules could be increased. This could be accomplished, for example, by permitting the administration of lower dosages of these molecules or by extending the range of tumors or viruses that these molecules can be used against.

The effectiveness of some chemotherapeutic agents has been enhanced by increasing the sensitivity of cells to such agents. For example, transduction of tumor cells by the herpes simplex thymidine kinase (hstk) gene has sensitized certain cells to agents which are not otherwise effective. Hstk phosphorylates, and thereby activates, nucleoside analogs such as ganciclovir (GCV) and acyclovir (ACV) [Moolten, F. L., *Cancer Res.* 46:5276–5281 (1986)]. Normal eukaryotic cells fail to phosphorylate GCV and are therefore relatively resistant to the drug. In contrast, those cells transduced with hstk convert GCV/ACV to the lethal phosphorylated intermediate. The identification of other chemosensitization gene/prodrug systems would be very valuable.

SUMMARY OF INVENTION

We have now identified a new method for enhancing the effectiveness of a group of molecules that are phosphorylated or capable of phosphorylation by dCK. Thus, we have identified a new chemosensitization "gene/prodrug" system. This system involves using dCK as the gene and molecules activated by dCK phosphorylation as the prodrug. The molecules that can be used are those that can be used against leukemia cells. These molecules include ara-C [Durham, J. P., et al., *Mol Pharmacol.,* 5:358–375 (1969); Ho. D. H. W., et al., *Cancer Res.* 33:2816–20 (1973); Habteyesus, A., et al., *Biochem. Pharmacol.* 42:1829–1836 (1991); Datta, N. S., et al., *Biochemistry* 28:114–123 (1989); Durham, J. P., et al., *J. Biol. Chem.,* 245:2276–2284 (1970); Erickson, S., et al., *Biochem. Biophys. Res. Commun.,* 176:586–592 (1991)], dFdC [Heinemann, V., et al., *Cancer Res.,* 48:4024–4031 (1988)], cladribine [Sarup, J. C., et al., *Biochem. Pharmacol.* 38:2601–2607 (1989)], zalcitabine [Datta, N. S., et al., *Biochemistry* 28:114–123 (1989); Srup, J. C., et al., *Biochem. Pharmacol.,* 38:2601–2607 (1989); Erickson, S., et al., *Biochem. Biophys. Res. Commun.,* 176:586–592 (1991)], and fludarabine [Tseng W., et al., *Mol Pharmacol.,* 21:474–477 (1982)]. Phosphorylization of these molecules yields the corresponding nucleoside triphosphate which exhibits an antiviral, antineoplastic, etc. activity.

One preferred way of increasing the effectiveness of these molecules is by increasing the sensitization of the target cells to these molecules. That can be accomplished by increasing the levels of dCK expressed. We have discovered that one way of accomplishing this is by introducing a dCK gene into a cell, e.g. by transducing a target cell with a gene encoding dCK, preferably the human dCK gene. Nucleic acid delivery systems include viral vectors, catheters, chemical conjugates, and fusion proteins having (1) a targeting moiety such as an antibody specific for a target cell and (2) a nucleic acid binding moiety such as a protamine. Preferably the dCK gene is operably linked to a promoter and more preferably also includes an element that results in a high level of expression. Preferably the gene is under the control of an inducible promoter.

BRIEF DESCRIPTION OF THE FIGURES

FIGS. 2A and 2B show sensitivity of retrofectants to the cytotoxic effects of ara-C. Cells were exposed to the indicated concentrations of ara-C for 24 h (FIG. 2A) or 96 hours (FIG. 2B) Cytotoxicity was determined by fixation, staining with methylene blue, and monitoring absorbance at 600 nm. Symbols: 9L (9L-WT) (○); 9L-Neo (□); and 9L-dCK (▲) cells. The results are expressed as the means+s.d. of eight experiments. The 9L-dCK cells were significantly more sensitive to ara-C than were either the 9L-WT or 9L-Neo cells ($P<0.001$; t-test).

FIG. 3A shows the effect of ara-C on mixtures of dCK-expressing and nonexpressing glioma cells. dCK-expressing and nonexpressing glioma cells were mixed at various ratios, plated in tissue culture dishes at $1 \times 10^5$ cells/plate, and then exposed to ara-C (200 nM). Surviving cells were then counted 3 days later. Data represent means+s.e.m. (bars) of two separate experiments expressed as percentage of total cell survival exposed to ara-C (□) compared with control cells not (■) exposed to ara-C. FIG. 3B shows the requirement for direct cell-to-cell contact for bystander effect. 9L-Neo cells were plated on the bottom of transwell microtiter plates and were either directly mixed with 9L-dCK-expressing cells or separated from dCK-expressing cells by a 3.0 µm membrane. Cells were then treated with ara-C at a dose of 200 nM. Data represent the means +s.e.m. (bars) of five separate experiments.

FIG. 4A shows 9L-Neo or 9L-dCK cells ($10^6$) that were inoculated intradermally on day 0. After the establishment of a small tumor nodule, rats were treated (T) with PBS or ara-C. Symbols represent 9L-Neo tumor-bearing rats treated with PBS (○) or ara-C (●), and 9L-dCK rats treated with PBS (□) or ara-C (■). The results are expressed as the mean+s.d. of tumor size in five rats. The difference in size of the 9L-dCK tumors treated with ara-C compared with the other groups was highly statistically significant ($P<0.001$). In FIG. 4B Kaplan-Meier curves demonstrate survival of rats with intracerebral tumors. 9L-Neo or 9L-dCK cells ($2 \times 10^4$) were stereotaxically injected into right caudate nucleus of the brain. Rats were treated with PBS or ara-C on days 2–3 and 10–11 (T), and survivals were monitored and plotted (n=8). Symbols represent 9L-Neo injected rats treated with PBS (○) or ara-C (●) and 9L-dCK rats treated with PBS (□) or ara-C (■). All the surviving rats were kept alive for more than 120 days. Survival of 9L-Neo animals treated with ara-C was statistically greater than PBS-treated animals by log rank analysis ($P<0.02$). The survival of 9L-dCK animals treated with ara-C was greater than the 9L-Neo plus ara-C group ($P<0.0005$).

FIGS. 5A and 5B show northern analysis of dCK expression in 9L cells transduced with the Ad.CMVdCK. In FIG. 5A forty-eight hours after transduction, cells were harvested and total RNA (20 µg) was analyzed for the expression of transgenes. In FIG. 5B 9L cells were transduced at the indicated MOIs in order to assess the effect of viral titer on the level of gene expression. Hybridization to the β-actin probe demonstrated equal loading of the lanes.

(FIG. 6A) Ad.CMVβgal at MOI 0 (●), 50 (■), 500 (▲); and (FIG. 6B) Ad.CMVdCK at MOI 0 (○), 50 (□) and 500 (▲). After 48 h, cells were exposed to the indicated concentrations of ara-C for 24 h. Cytotoxicity was determined by staining with methylene blue. The results are expressed as the means+s.d. of eight experiments (bars+s.d.). The difference in cell killing was highly statistically significant for cells treated with Ad.CMVdCK at an MOI of 500 (P<0.00 1).

DETAILED DESCRIPTION OF INVENTION

Figure 1:
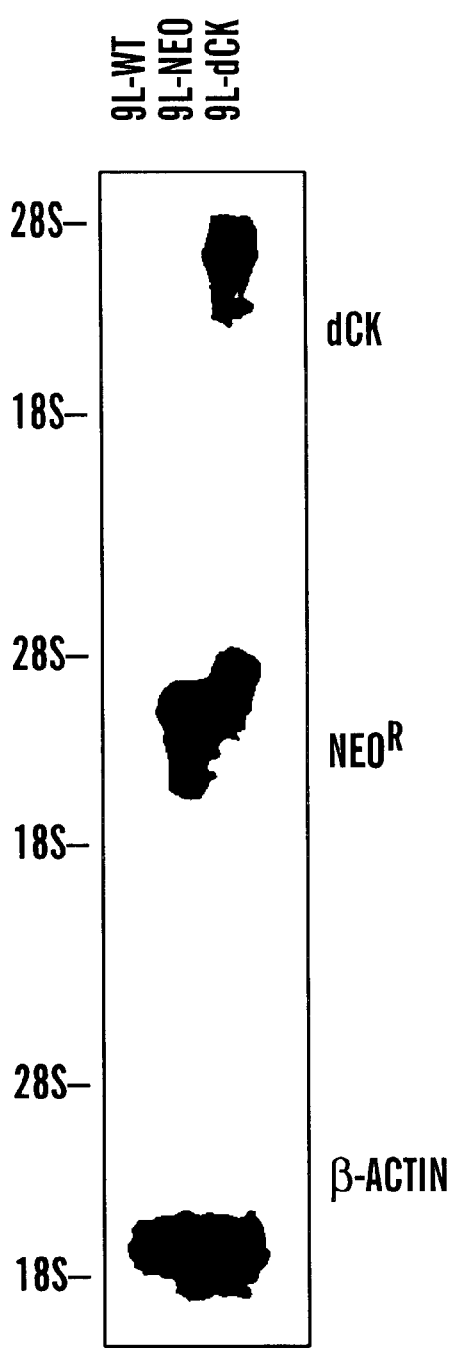
FIG. 1 shows dCK-Specific mRNA expression in pMV7-dCK retrofectants. Total RNA (20 µg) was analyzed for expression of the transgenes by northern analysis. The full-length dCK cDNA was used to probe for expression of dCK mRNA. The neomycin 3' phosphotransferase (neo$^R$) cDNA was used as a control to show expression of neo$^R$ mRNA in both 9L-Neo and 9L-dCK cells. Hybridization to the β-actin probe demonstrates equal loading of the lanes.

The effectiveness of molecules that are phosphorylated or capable of phosphorylation by dCK can be enhanced by increasing the level of dCK in a target cell. A target cell is any cell, preferably any human cell, where you want to increase its sensitivity to an activated dCK-phosphorylated molecule.

We have discovered that the level of dCK in a cell can be increased by introducing a dCK gene into the cell.

Preferably, the dCK gene is a mammalian dCK gene, still more preferably it is a human dCK gene [Song, J. J., et al., Proc. Natl. Acad. Sci. USA, 90:431–434 (1993); Chottiner, E. G., et al., Proc. Natl. Acad. Sci. USA, 88:1531–1535 (1991); Karlsson, A., et al., Pharm. World Sci., Suppl F:F19 (1993); Datta, N. S., et al., Biochemistry 28, 114–23 (1989)]. The dCK gene does not have to be the full length wild type gene, but it must encode a functional dCK protein. As used herein "functional" means a protein having at least 70% dCK wild-type activity in phosphorylating a molecule capable of being phosphorylated by the dCK protein. This activity can be determined by a number of assays using known techniques based upon the present disclosure. For example, ara-C is converted to its active form via a phosphorylation pathway that includes dCK, deoxycytidylate (dCMP) kinase, and nucleoside diphosphate (NDP) kinase. Typically dCK is rate limiting in the pathway.

One can prepare dCK transduced cells, such as glioma cells. For example, one can use a retroviral vector (e.g. a murine moloney leukemia virus such as pMV7), an adenoviral vector, a herpes simplex viral vector, etc. to transduce a glioma cell line (e.g. the 9L gliosarcoma cell line). As a control, a mock transfected glioma cell line, a marker-transfected cell line or reference standard can be used. The transduced cells can then be implanted into an animal model such as a rat by known techniques. Thereafter, ara-C can be administered and the tumor volume monitored over time (see FIG. 4). By this means the phosphorylation activity of wild-type dCK can be established and mutant dCK genes screened to determine whether they encode a functional dCK protein. Using known techniques one can make deletions, substitutions or insertions in the gene. Preferably, the substitutions result in conservative amino acid substitutions. Such conservative substitutions are known in the art. The mutant dCK gene can readily be tested in the above model and compared with a reference standard. Preferably one uses a dCK gene encoding a full-length wild type dCK protein.

The target cells include any cells which can be sensitized by dCK and treated by an activated dCK phosphorylated molecule. For example, there are a number of molecules discussed more fully below that are activated by dCK to exhibit a desired effect such as a therapeutic effect, e.g. an antiviral or antineoplastic effect. Ara-C is one such molecule. In its activated form it exhibits an antineoplastic effect, particularly against leukemias. We have found that the ara-C activity can be extended to other cancers such as solid tumors, preferably breast, kidney, liver, brain and colon cancers. More preferably, the tumor is a brain tumor such as glioma.

Preferred target cells include malignant and/or virally infected cells. Examples of malignant cells include solid tumors such as brain tumors, breast tumors, kidney tumors, liver tumors, colon tumors, etc. Preferred solid tumors include brain tumors such as gliomas. Virally infected cells include infected CD4 cells such as HIV-infected cells.

One can readily determine if a cell is an appropriate target tissue for a molecule by introducing a dCK gene into that cell, adding a prodrug molecule to that cell and determining if the prodrug in the cell displays an enhanced sensitivity, e.g. an antiviral or antineoplastic effect which is at least 20%, more preferably at least 30%, still more preferably at least 50%, and even more preferably at least 75%, greater than the prodrug displays in the corresponding non-dCK transduced cell or cell line. Desired target cells will vary depending upon the prodrug molecule being employed and this can be empirically established by the above-mentioned assays.

The dCK gene can be introduced into the target cell by any method which will result in the uptake and expression of the dCK gene by the target cells. These can include vectors, liposomes, naked DNA, adjuvant-assisted DNA, catheters, etc. Vectors include chemical conjugates such as described in WO 93/04701, which has a targeting moiety (e.g. a ligand to a cellular surface receptor) and a nucleic acid binding moiety (e.g. polylysine), viral vectors (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses and HIV-based viruses. One preferred HIV-based viral vector comprises at least two vectors wherein the gag and pol genes are from an HIV genome and the env gene is from another virus. DNA viral vectors are preferred. These vectors include pox vectors such as orthopox or avipox vectors, herpesvirus vectors such as a herpes simplex I virus (HSV) vector [Geller, A. I. et al., *J. Neurochem,* 64: 487 (1995); Lim, F., et al., in DNA Cloning: *Mammalian Systems,* D. Glover, Ed. (Oxford Univ. Press, Oxford England) (1995); Geller, A. I. et al., *Proc Natl. Acad. Sci.: U.S.A.:*90 7603 (1993); Geller, A. I., et al., *Proc Natl. Acad. Sci USA:* 87:1149 (1990)], adenovirus vectors [LeGal LaSalle et al., *Science,* 259:988 (1993); Davidson, et al., *Nat. Genet* 3: 219 (1993); Yang, et al.,*J. Virol.* 69: 2004 (1995)] and adeno-associated virus vectors [Kaplitt, M. G., et al., *Nat. Genet.* 8:148 (1994)].

Pox viral vectors introduce the gene into the cells cytoplasm. Avipox virus vectors result in only a short term expression of the dCK gene. Adenovirus vectors, adeno-associated virus vectors and herpes simplex virus (HSV) vectors are preferred for introducing the dCK gene into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include naked DNA, $CaPO_4$ precipitation, DEAE dextran, electroporation, protoplast fusion, lipofection, cell microinjection, viral vectors, etc.

For example, one can use the vector to target any desired target cell such as a glioma. For example, stereotaxic injection can be used to direct the vectors (e.g. adenovirus, HSV) to a desired location in the brain (e.g. a glioma). Stereotaxic surgery is performed using standard neurosurgical procedures (Pellegrino and Cushman, (1971)). Additionally, the particles can be delivered by intracerebroventricular ("icv") infusion using a minipump infusion system, such as a SynchroMed Infusion System. A method based on bulk flow, termed convection, has also proven effective at delivering large molecules to extended areas of the brain and may be useful in delivering the vector to the target cell (Bobo et al., *Proc. Natl. Acad. Sci. USA* 91:2076–2080 (1994); Morrison et al., *Am. J. Physiol.* 266: 292–305 (1994)). Other methods that can be used include catheters, intravenous, parenteral, intraperitoneal and subcutaneous injection, oral or other known routes of administration.

Figure 6B:
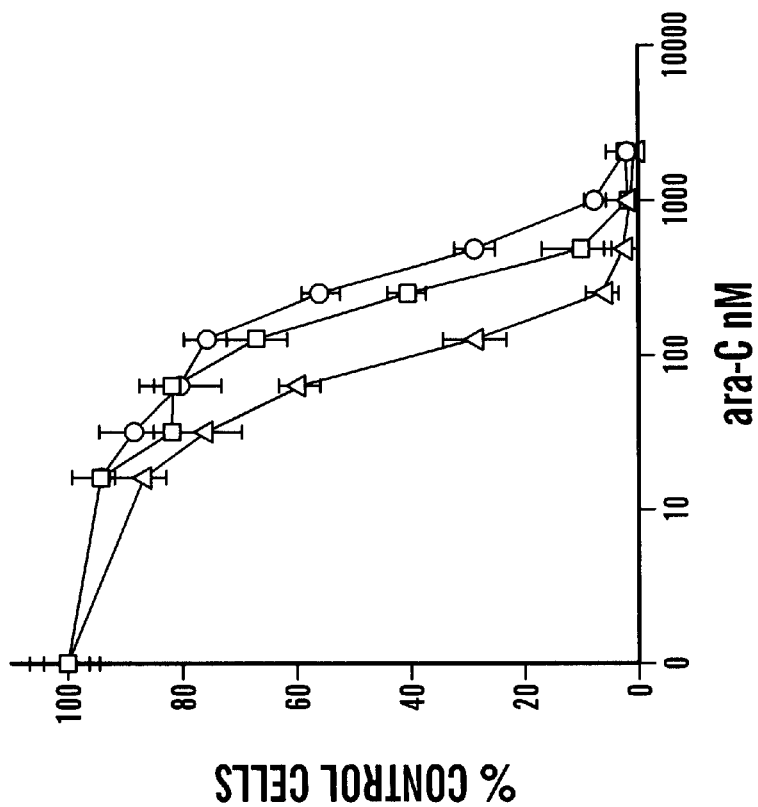
FIGS. 6A and 6B show in vitro sensitivity to ara-C following transduction with dCK-expressing or control virus. 9L cells ($2 \times 10^3$) were infected as follows.

One would inject a sufficient amount of the vector to obtain a concentration in the dCK target cell ranging between about 1 pg/ml to 20 μg/ml. More preferably between 0.1 μg/ml to 10 μg/ml. Still more preferably, between about 0.5 μg/ml to 10 μg/ml.

dCK catalyzes the phosphorylation of a range of pyrimidine and purine deoxynucleotides to the corresponding nucleotide. Many of those nucleotides display an effect which can be useful in "treating" a target cell. For example, many of these prodrug molecules, when activated exhibit an antiviral, preferably an anti-retroviral effect [Balzarini, J., *Pharm. World Sci.,* 16, 113–26 (1994)]. In another preferred embodiment many of the prodrug molecules exhibit an antineoplastic effect. Preferred examples include ara-C, aza-CdK, dFdC, cladribine, zalcitabine and fludarabine. Ara-C although effective in treating leukemias has only shown limited activity against most solid tumors. We have shown that ara-C's effectiveness can be enhanced when a dCK gene is introduced into a target cell. For example, introducing a dCK gene into a solid tumor such as a glioma can make that target cell more sensitive to the anti-neoplastic effect of ara-C (see FIG. 6A and FIG. 6B).

The prodrug compositions may be employed alone or in combination with acceptable carriers such as those described below. For the treatment of viral infections, for example, an HIV infection, combination therapy is particularly preferred. Suitable effective dose of the prodrug in a composition will be in the range of 1 to 5,000 µg per kilogram body weight of recipient per day, preferably in the range of 10 to 4,000 µg per kilogram body weight of recipient per day.

The prodrug molecule may be administered alone, or as part of a pharmaceutical composition, comprising at least one prodrug together with one or more acceptable carriers thereof and optionally other therapeutic ingredients. The carrier(s) must be "acceptable" in the sense of being compatible with the other ingredients of the formulation and not deleterious to the recipient thereof.

The compositions include those suitable for oral, rectal, nasal, topical (including buccal and sublingual), vaginal or parenteral (including subcutaneous, intramuscular, intravenous and intradermal) administration. The formulations may conveniently be presented in unit dosage form, e.g., tablets and sustained release capsules, and in liposomes, and may be prepared by any methods well know in the art of pharmacy.

Such methods include the step of bringing into association with the molecule to be administered ingredients such as the carrier which constitutes one or more accessory ingredients. In general, the compositions are prepared by uniformly and intimately bringing into association the active ingredients with liquid carriers, liposomes or finely divided solid carriers or both, and then if necessary shaping the product.

Compositions of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Compositions suitable for topical administration include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Compositions suitable for a topical administration to the skin may be presented as ointments, creams, gels and pastes comprising one or more compounds of the present invention and a pharmaceutically acceptable carrier. A suitable topical delivery system is a transdermal patch containing the ingredient to be administered.

Compositions suitable for rectal administration may be presented as a suppository with a suitable base comprising, for example, cocoa butter or a salicylate.

Compositions suitable for nasal administration wherein the carrier is a solid include a coarse powder having a particle size, for example, in the range 20 to 500 microns which is administered in the manner in which a compound is inhaled, i.e., by rapid inhalation through the nasal passage from a container of the powder held close up to the nose. Suitable formulations wherein the carrier is a liquid, for administration, as for example, a nasal spray or as nasal drops, include aqueous or oily solutions of the active ingredient.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets of the kind previously described.

It should be understood that in addition to the ingredients particularly mentioned above the formulations of this invention may include other agents conventional in the art having regard to the type of formulation in question, for example, those suitable for oral administration may include flavoring agents.

For example, solid dose forms that can be used for oral administration include capsules, tablets, pills, powders and granules. In such solid dose forms, the active ingredient, i.e., the dCK gene and/or prodrug molecule is mixed with at least one insert carrier such as sucrose, lactose or starch. Such dose forms can also comprise additional substances other than inert diluents, e.g., lubricating agents, such as magnesium stearate. Furthermore, the dose forms in the case of capsules, tablets and pills may also comprise buffering agents. The tablets, capsules and pills can also contain time-release coatings to release the particles over a predetermined time period.

For parenteral administration, one typically includes sterile aqueous or non-aqueous solutions, suspensions or emulsions in association with a pharmaceutically acceptable parenteral vehicle. Examples of non-aqueous solvents or vehicles are propylene glycol, polyethylene glycol, vegetable oils such as olive oil and corn oil, gelatin and injectable organic esters, such as ethyl oleate. These dose forms may also contain adjuvants such as preserving, wetting, emulsifying and dispersing agents. They may be sterilized by, for example, filtration through a bacterial-retaining filter, by incorporating sterilizing agents into the composition, by irradiating the compositions, etc., so long as care is taken not to inactivate the active ingredient (e.g. a vector). They can also be manufactured in a medium of sterile water or some other sterile injectable medium before use. Further examples of these vehicles include saline, Ringer's solution, dextrose solution and 5% human serum albumin. Liposomes may also be used as carriers. Additives, such as substances that enhance isotonicity and chemical stability, e.g., buffers and preservatives, may also be used.

The preferred range of active ingredient in such vehicles is in concentrations of about 1 mg/ml to about 10 mg/ml. More preferably, about 3 mg/ml to about 10 mg/ml.

The present invention is further illustrated by the following Examples. These Examples are provided to aid in the understanding of the invention and are not construed as a limitation thereof.

Incorporation of ara-C into DNA and Nucleotide Pools

We measured incorporation of ara-C into DNA and cellular pools of the active intermediate of ara-C metabolism, ara-CTP and thereby established whether high levels of dCK expression correlate with increased metabolic activation of ara-C. Then, 9L-WT, 9L-Neo, or 9L-dCK cells were treated with [$^3$H]ara-C for 3 and 6 hours, and incorporation of ara-C into DNA was assayed. A three-to sevenfold increase in the amount of ara-C incorporated into DNA was seen in the 9L-dCK cells compared with control cells (P<0.002 and P<0.02 at 3 and 6 hours, respectively; Table 1). No significant difference was observed between 9L-WT and 9L-Neo cells.

Because ara-CTP is the active metabolite that is incorporated into DNA, total ara-CTP pools were determined by high-performance liquid chromatography (HPLC) using an AX10 anion-exchange column. In 9L-dCK cells, ara-CTP as well as ara-CMP/ara-CDP pools were approximately two times as high as those in 9L-WT or 9L-Neo cells after 3 hours treatment with [$^3$H]ara-C (P<0.002; Table 2).

Bystander Effect in 9L-dCK Cells

Figure 3B:
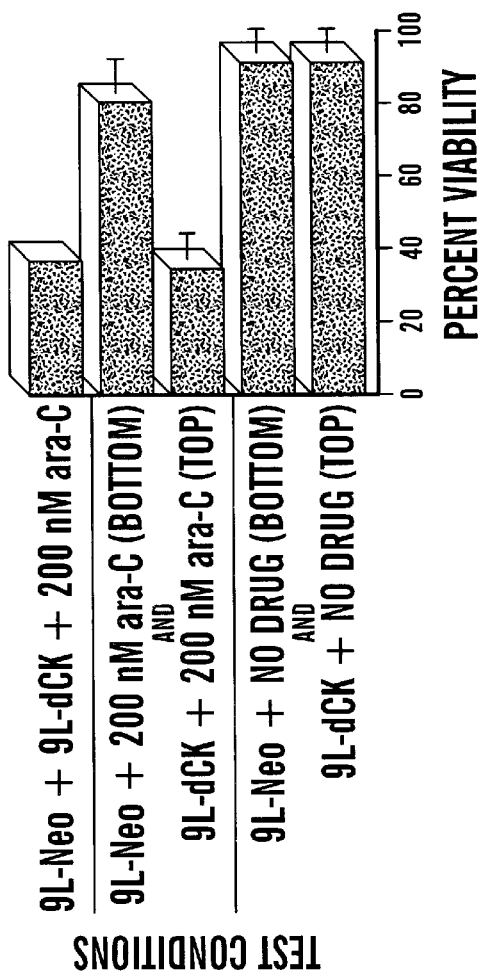
FIGS. 3A and 3B, show dCK-mediated bystander effect following ara-C exposure.
Figure 3A:
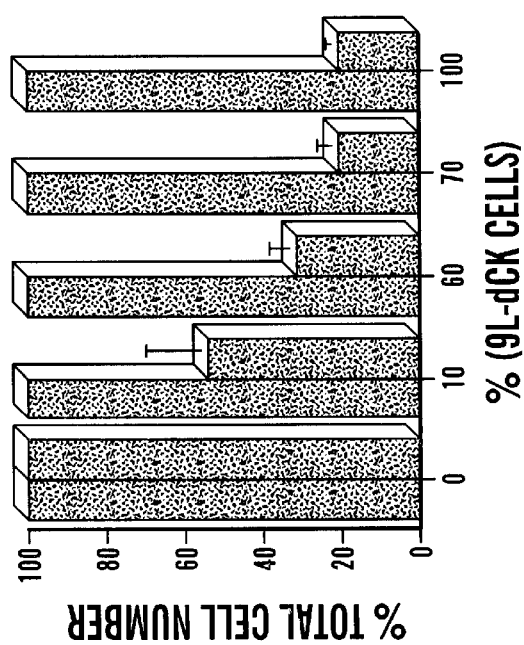

We next evaluated whether this dCK/ara-C system is associated with a bystander effect such that nontransduced wild-type cells adjacent to dCK-expressing cells become sensitive to ara-C. Cells were mixed at different ratios of 9L-Neo and 9L-dCK and then exposed to a concentration of ara-C that is not toxic to 9L-Neo cells. Nearly 50% or 70% of the total cell population was killed following ara-C exposure when 9L-Neo cells were mixed with 10% or 50% of 9L-dCK cells, respectively (FIG. 3a). These results suggest that, although a bystander effect appears to exist, the effect in this system was relatively minimal.

In order to determine whether the dCK/ara-C-mediated bystander effect is dependent on direct cell-to-cell contact, 9L-Neo cells were plated on the bottom of a microliter transwell either directly with 9L-dCK cells or separated from the 9L-dCK cells by a 3-μm porous membrane. Significant cytotoxicity (38%+2% of control) was also seen in the 9L-Neo cells that were directly mixed in the bottom compartment with the 9L-dCK cells, compared with minimal cytotoxicity (81% of control) when the 9L-Neo cells were separated from the 9L-dCK cells by the membrane (FIG. 3b). The difference in cytotoxicity between cell-to-cell and membrane separated cell killing was statistically significant; P<0.01. After 5 days of culture in the microliter transwell plates, 91% of 9L-Neo and 9L-dCK not exposed to ara-C remained viable. These findings demonstrate the dependence of the small dCK/ara-C bystander effect on direct cell-to-cell contact and suggest that a freely diffusible molecule (one that can pass through the 3-μm porous membrane) is not responsible for the collateral cell sensitization to ara-C.

Growth of 9L-dCK in Syngeneic Rat

Figure 4B:
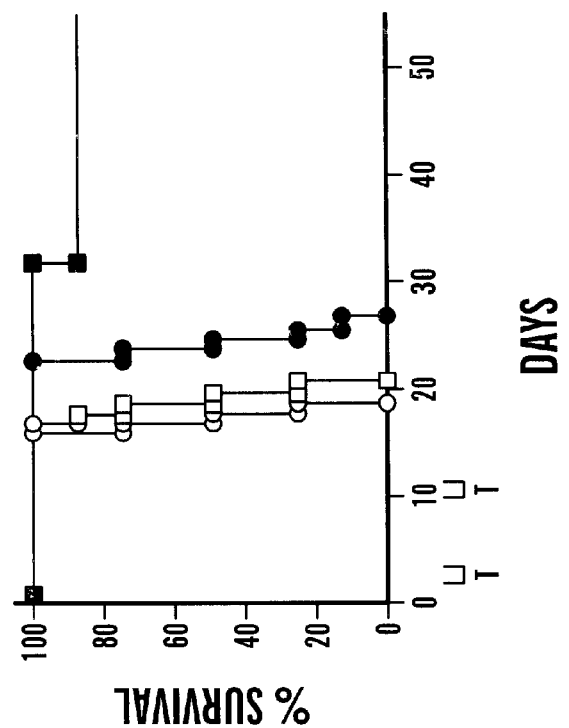
FIGS. 4A and 4B show in vivo growth of intradermal and intracerebral retrofected gliomas treated with ara-C.
Figure 4A:
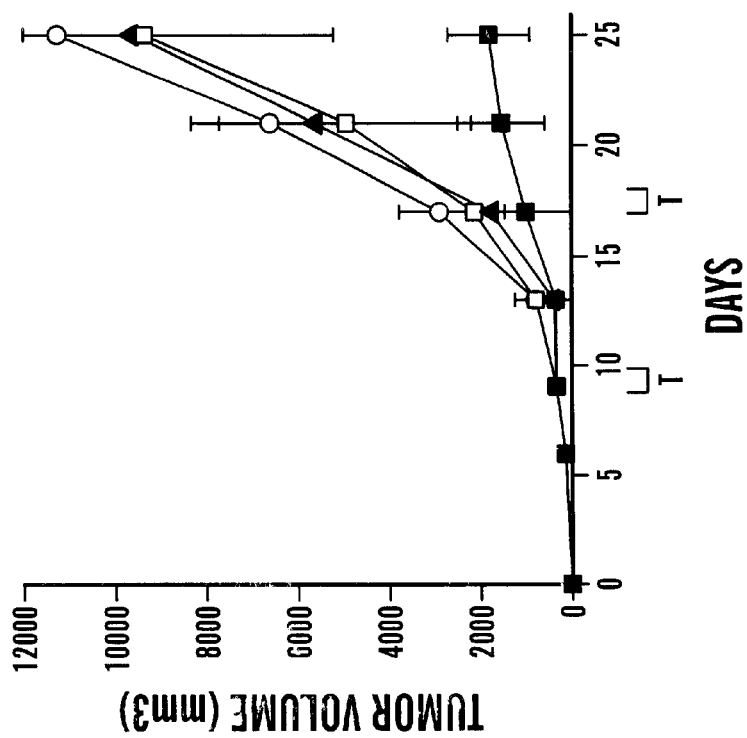

Based on the encouraging in vitro data, we proceeded to evaluate the in vivo sensitivity of these cell lines using both intradermal and intracerebral tumor models. In the first experiment, $10^6$ 9L-Neo or 9L-dCK cells were inoculated into the right flank of Fischer 344 rats. On day 9, when small tumor nodules were present, rats were treated with ara-C or phosphate-buffered saline (PBS). The dose of ara-C used in these studies was 200 mg/kg body weight, a dose previously shown to be equivalent to "high-dose" ara-C (1 g/m$^2$) in humans [11–14]. There was no significant difference in the growth of 9L-Neo tumors as a result of ara-C or PBS administration (FIG. 4a). In contrast, ara-C treatment resulted in significantly smaller 9L-dCK tumors than did PBS treatment (1791+894 mm$^3$ versus 9317+4147 mm$^3$, respectively; P<0.001). Also, ara-C treatment of dCK tumors resulted in significantly smaller tumors than that obtained for ara-C-treated 9L-Neo tumors (1791+894 mm$^3$ versus 9556+2272 mm$^3$, respectively; P<0.00 1).

In a second experiment, intracerebral tumors were established and rat survival was measured. Secondary to restricted intracranial volume, the survival of rats in this model represents a very reproducible parameter for determining the growth of transplanted tumors or tumor cell lines in vivo. There was no significant difference in survival of animals harboring 9L-Neo or 9L-dCK tumors when treated with PBS (FIG. 4B). In contrast, when animals with the 9L-Neo tumors were treated with ara-C, there was a significant 8-day prolongation of median survival compared with the PBS-treated animals (P<0.02). When animals with 9L-dCK tumors were treated with ara-C, however, seven of eight rats were cured of their tumors (survival>120 days; P<0.0005). Histologic evaluation of the brains of long-term survivors revealed only a small area of necrosis, and no viable tumor in any of the tissue sections.

Gene Transfer Experiments Using an Adenoviral Vector System

Based on our data demonstrating that dCK gene expression facilitates ara-CTP formation and enhanced ara-C sensitivity to 9L cells both in vitro and in vivo, we expect that dCK is an effective chemosensitization gene for gene therapy. We constructed a replication-deficient recombinant adenovirus carrying the CMV promoter-dCK gene minicassette (Ad.CMVdCK) to further establish this. To test that activity of this vector, 9L wild-type cells were transduced with either Ad.CMVβgal or Ad.CMVdCK in vitro. Forty-eight hours later, total RNA was harvested and analyzed for expression of the transgene. The 9L cells transduced with Ad.CMVdCK expressed high levels of dCK mRNA, seen as a lower band resulting from transcriptional termination at the SV-40 polyadenylation signal (contained within the minigene cassette) and a higher band resulting from SV-40 polyadenylation signal read through with termination at one of the endogenous adenoviral E1A polyadenylation signals. In contrast, dCK expression was low to undetectable in Ad.CMVβgal infected cells (FIG. 5a). Levels of dCK expression were dependent on the multiplicity of infection (MOI) (FIG. 5b).

Figure 6A:
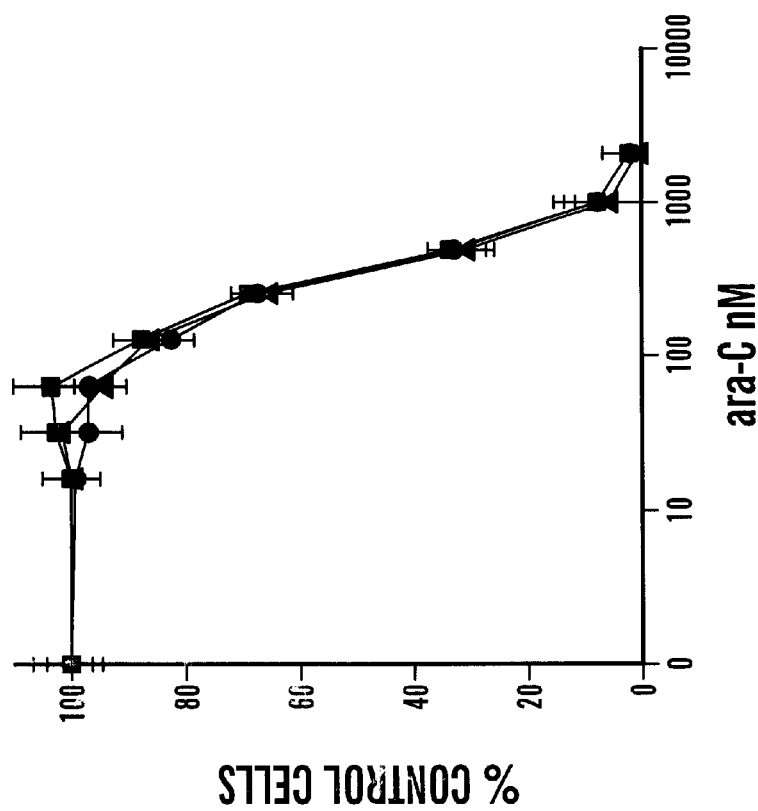

Cytotoxic assays were performed to determine whether 9L transduction by Ad.CMVdCK confers ara-C sensitivity. Forty-eight hours after transduction, 9L cells were exposed to various concentrations of ara-C for 24 hours. Forty-eight hours later, cells were assayed for cytotoxic effects. The 9L cells transduced by Ad.CMVβgal at different MOIs demonstrated no difference in sensitivity to ara-C with an IC$_{50}$ of approximately 300 nM (FIG. 6A). In contrast, 9L cells transduced by Ad.CMVdCK exhibited an MOI-dependent increase in sensitivity as demonstrated by IC$_{50}$ values of 300 nM, 190 nM and 80 nM, for MOIs of 0,50 and 500, respectively (FIG. 6b) (P<0.001 for MOI of 500 compared with MOIs of 50 and 0).

Figure 7:
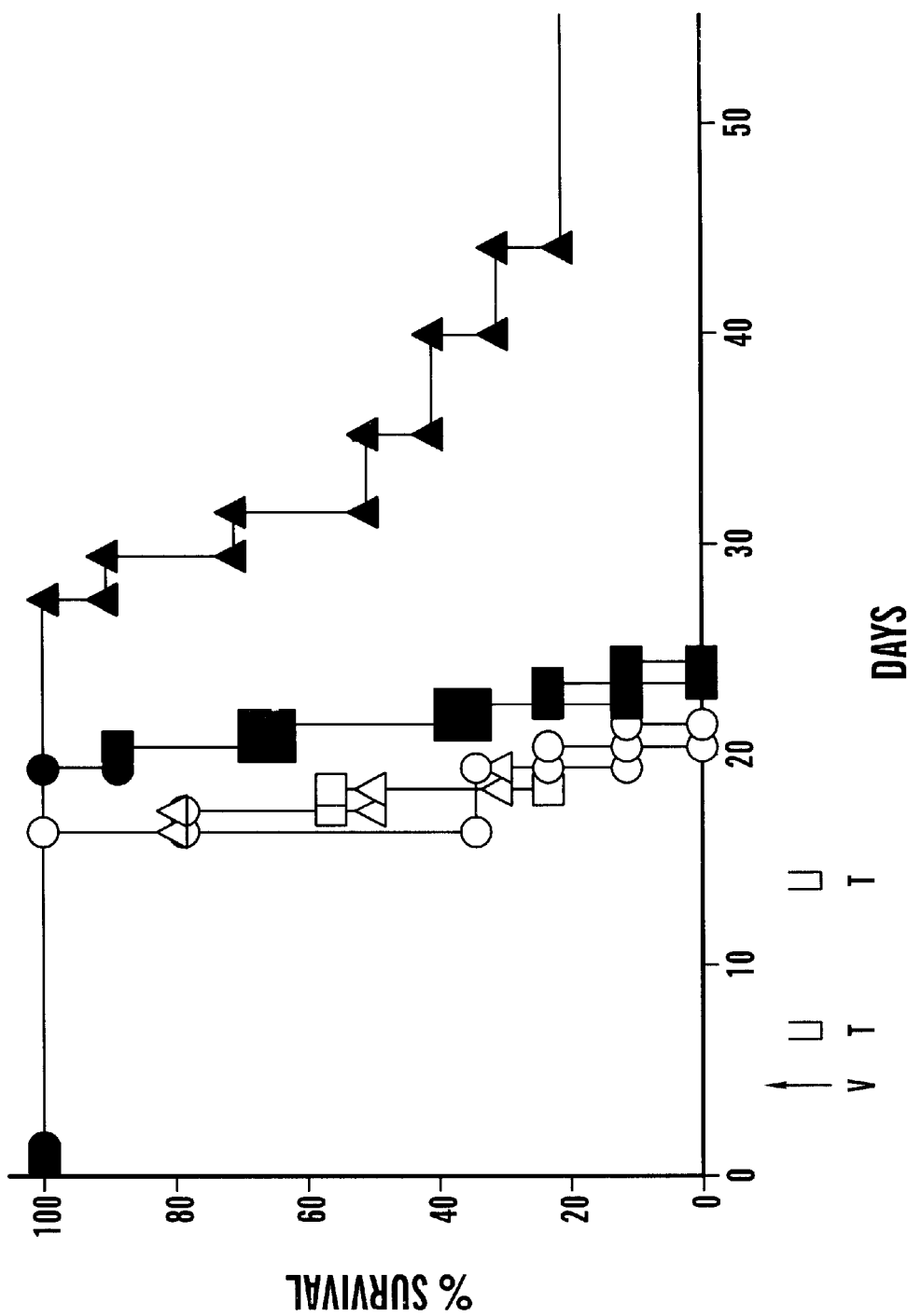
FIG. 7 shows animal survival following in vivo transduction of established gliomas by control or dCK-expressing adenoviral vector. Kaplan Meier curves are shown for intracerebral tumors treated with recombinant adenoviral vectors. 9L-Neo or 9L-dCK cells ($2 \times 10^4$) were injected into right caudate nucleus of the brain. Four days later, viral vehicle or $2 \times 10^8$ PFU of recombinant adenoviruses were injected into the tumors stereotaxically using the same route of previous 9L inoculation (V). Forty-eight hours later, rats were treated with PBS or ara-C (T), and survival was monitored and recorded on the Kaplan-Meier survival curve. Vehicle injection and treatment with PBS (○, n=8), or ara-C (●, n=9), Ad.CMVβgal infection and treatment with PBS (□, n=9) or ara-C (■, n=9), Ad.CMVdCK injection and treatment with PBS (_, n=10), or ara-C (▲, n=10). The survival of animals injected with vehicle and Ad.CMVβgal and treated with ara-C was similar to each other and significantly longer than those treated with PBS (P<0.01). Survival of Ad.CMVdCK/ara-C-treated animals, however, was statistically greater than any other treatment groups (p<0.0005).

The ability of Ad.CMVdCK to mediate expression of dCK messenger RNA in vivo was confirmed by northern analysis, which demonstrated an appropriate-sized mRNA signal in rat brains transduced by Ad.CMVdCK compared with no signal from control vector-transduced brains (data not shown). In order to evaluate whether in vivo transduction of an established intracerebral glioma by Ad.CMVdCK could sensitize the tumor cells to ara-C, $2\times10^4$ 9L cells were injected stereotaxically into the right caudate nucleus of the brain of syngeneic Fischer 344 rats. Four days later, viral vehicle, or $2\times10^8$ PFU (plaque-forming units) of either the Ad.CMVβgal or Ad.CMVdCK vectors were stereotactically injected into the tumors. Forty-eight hours later, rats were treated with either PBS or ara-C. There was no difference in survival among vehicle, Ad.CMVβgal and Ad.CMVdCK-injected rats treated with PBS (all animals were dead by day 21) (FIG. 7). Survival between the vehicle and Ad.CMVβgal injected animals that were treated with ara-C was similar and longer than that seen in the PBS-treated animals ($P<0.02$). Animals treated with Ad.CMVdCK and ara-C, however, survived much longer than animals treated with the viral vehicle or Ad.CMVβgal and ara-C ($P<0.0005$) (FIG. 7).

Transduction of genes that sensitize tumor cells to prodrugs represents a significant strategy for cancer gene therapy. We have demonstrated that introduction of the dCK gene into a target cell as exemplified by transduction and expression of the dCK gene enhances the ability of glioma cells to metabolize ara-C to its active intermediates. This approach results in a significant increase in sensitivity to ara-C in vitro and in vivo.

Role of dCK in Intracellular ara-C Metabolism.

Ara-C penetrates cells by a carrier-mediated process using a nucleoside transporter that binds nitrobenzylthionosine [Wiley, J. S. et al. *J. Clin. Invest.* 69, 479–489 (1982)]. Ara-C is converted to its active form via phosphorylation by three successive enzymes including dCK, deoxycytidylate (dCMP) kinase, and nucleoside diphosphate (NDP) kinase. The active intermediate of ara-C metabolism is ara-CTP, which mediates its cytotoxic effects by incorporating into replicating DNA, an event that directly correlates with cytotoxicity [Kufe, D., et al., *J. Biol. Chem.* 225:8997–9000 (1980); Fram, R. J., et al. *Leuk. Res.* 7:243–249 (1983)]. Ara-CTP incorporation into DNA results in template dysfunction and chain termination [Kufe, D. W. et al. *Mol Pharmacol.* 26:128–134 (1984); Mikita, T. et al. *Biochemistry* 27:4698–4705 (1988); Ohno, Y. et al. *Cancer Res.* 48:1494–1498 (1988)]. The cytotoxic effects of ara-C can be abrogated by blocking this incorporation of ara-CTP into DNA. Alternately, ara-C can be metabolized to inactive intermediates directly through the action of cytidine deaminase or indirectly through the inactivation of ara-CMP by a dCMP deaminase. Thus, ara-C activation depends on a relative balance between activating and degradative enzymes. dCK is believed to be the rate-limiting step in prodrug activation such as ara-C activation [Plagemann, P. G. W. et al. *Cancer Res.* 38, 978–989 (1978)]. We have shown that ara-C metabolism could be shifted from intracellular deamination toward phosphorylation and activation following overexpression of dCK. Our in vitro data demonstrated that transduction of the dCK cDNA results in increased sensitivity to the cytotoxic effects of ara-C. Moreover, dCK transduction was associated with accumulation of intracellular ara-C nucleotide pools and increased levels of ara-C incorporation into DNA.

Our data also demonstrate that overexpression of the dCK gene can greatly enhance ara-C induced cytotoxicity in vivo. These studies were performed at ara-C doses (200 mg/kg) comparable to high dose schedules used in humans [Colly, L. P. et al. *Med. Pediatr. Oncol.* 209 (suppl.1) 209–220 (1982); Colly, L. P. et al. *Cancer Res.* 46:3825–3827 (1986); Colly, L. P. et al. *Leuk. Res.* 8:945–952 (1984); Vaughan, W. P. et al. *Cancer Res.* 43:2005–2009 (1983)]. Although there are a number of dose schedules that have been used for the administration of ara-C, we chose to use an intermittent high-dose schedule based on pharmacokinetics principles of drug delivery to intracerebral tumors. For drugs like ara-C that are water-soluble and can permeate the blood-brain barrier, intrabrain parenchyma and cerebrospinal fluid (CSF) concentrations of drug correlate with peak serum concentrations. Thus, the higher the serum concentration, the greater the exposure of intracerebral tumors to ara-C. It stands to reason, therefore, that high-dose regimens should be capable of producing higher intracerebral concentrations of ara-C than lower dose, continuous infusion regimens. Based on these principles, it is also reasonable to conclude that intra-arterial (intracarotid) administration of ara-C might be even more effective than subcutaneous administration, although the dose need to be adjusted as it is potentially more toxic. In addition to modifications in the route of ara-C administration, multiple treatments with a vector such as Ad.CMVdCK and ara-C should improve the antitumor efficacy of this approach. With multiple treatments care must be taken in the vector selection. For example, issues related to the inherent immunogenicity of the adenoviral vector, with the subsequent development of a neutralizing host immune response, effect its repeated use [Engelhardt, J. F. et al. *Nature Genet.* 4:27–34 (1993); Engelhardt, J. F. et al. *Proc. Natl. Acad. Sci. USA* 91:6196–6200 (1994)]. One may wish to use different vectors with repeated doses to avoid such an immune response. For example, adenovirus, HSV, pox, etc. Additionally, our in vitro data suggest that the dCK/ara-C bystander effect is low, possibly contributing to the lower survival in the Ad.CMVdCK-treated animals compared with the animals harboring the stably transfected glioma cells. The reason for the low-level bystander effect is unknown but may relate to inefficient transfer of the activated intermediate metabolites (ara-CDP, ara-CTP) across intracellular junctions and/or the rapid degradation of these intermediates. Additional in vivo experiments will help define optimal dose schedule of Ad.CMVdCK and ara-C for the treatment of malignant gliomas.

The 9L Glioma Model and Gene Transfer

A potentially complicating variable in these experiments is the fact that the 9L glioma model has been shown to be immunogenic in its syngeneic host [Tapscott, S. J. et al. *Proc. Natl. Acad. Sci. USA* 91:8185–8589 (1994)]. Other syngeneic glioma models exists (that is, C6, RT-2), however, these models are also immunogenic to their hosts, and are not as well characterized as the 9L model. We do not believe that the immune response impacted significantly on the results of our in vivo experiments for a number of reasons. First, all 9L transfectants grew in the immunocompetent animals regardless of whether they were transduced by the control or dCK-expressing retroviral vectors. Both subdermal tumors and intracranial tumors grew at the same rate as wild-type 9L cells regardless of which vector they were transduced with, and resulted in animal death at approximately the same time. For the adenoviral experiments, we controlled for the possibility that viral antigens could costimulate an effective antitumor immune response by not only comparing the survival of animals treated with PBS with those treated with ara-C but also by using a related adenoviral vector that does not express dCK (Ad.CMVβgal). These controls indicate that the principal mechanism of tumor cytotoxicity is dCK expression along with ara-C administration, although a minor contribution from an antitumor immune response cannot be ruled out.

The dCK/prodrug system, e.g. dCK/ara-C system, has a number of potential advantages for cancer gene therapy, particularly of central nervous system tumors. (1) The concentration of these prodrugs, e.g. ara-C, that is cytotoxic for dCK -transduced cells is well below the serum and CSF concentrations of ara-C that are achievable in humans; (2) Ara-C is one of the few agents that can be safely administered directly into the CSF of patients with tumor cell involvement of the leptomeninges; (3) Ara-C is a cell cycle-specific drug such that most of the cells within the CNS, which are postmitotic, should be relatively unaffected when transduced by dCK; (4) Finally, as opposed to hstk and other currently utilized chemosensitization genes, such as cytosine deaminase, dCK is a human gene and thus limits the chance for a significant anti-dCK immunologic response in humans. We believe that these advantages, coupled with our encouraging in vitro and in vivo data, indicate that dCK/ara-C system will result in a clinically useful approach for gene therapy of CNS-based neoplasms, as well as other solid tumors.

Tumor Cell Line and Animals

The 9L gliosarcoma cell line (provided by Peter Black, Brigham & Women's Hospital, Boston, Mass.) was maintained in DMEM containing 10% fetal bovine serum. The amphotropic PA317 retrovirus packaging cell line was purchased from the American Type Culture Collection (ATCC, Rockville, Md.) and grown in DMEM with 4.5 g/l glucose supplemented with 10% fetal bovine serum. Adult male Fischer 344 (CDF) rats (150–175 g) were purchased from Charles River Laboratories (Wilmington, Mass.).

Construction of dCK-expressing Vectors and Cell Lines

A 0.8-kb fragment of the human deoxycytidine kinase (dCK) cDNA (ref. 24) was cloned into the EcoRI site of the pMV7 retroviral vector (provided by Gerard M. Housey, Columbia University, New York). This plasmid was designated pMV7-dCK. In pMV7-dCK the dCK cDNA is located just 3', and transcribed from the murine Moloney leukemia virus long terminal repeat (LTR). The neo gene is transcribed from a thymidine kinase promoter (tk).

Supernatant from PA317/pMV7 or PA317/pMV7-dCK retroviral producer cells was used to transduce 9L target cells. The cells were incubated for 24 h and then selected for 2 weeks in the presence of 400 µg/ml (active drug) genecticin sulfate (Gibco BRL, Gaithersburg, Md.). Polyclonal populations of 9L-Neo (transduced by pMV7) and 9L-dCK (transduced by pMV7-dCK) cells were characterized for dCK expression by northern blot analysis.

Northern Blot Analysis

Total cellular RNA was obtained using guanidine isothiocyanate-cesium chloride purification [Chirgwin, J. M. et al. Biochemistry 18:5294–5299 (1979)]. The RNA (20 µg) was analyzed by electrophoresis through 1% agaroseformaldehyde gels, transferred to nitrocellulose paper, and hybridized to the following $^{32}$P-labeled DNA probes: (1) a 0.8-kb Ncol and Baml fragments of cDK from the pET3d-dCK plasmid; (2) a 1.3-kb HindIII's fragment from the p1Aneo plasmid containing the neomycin 3'-phosphotransferase cDNA sequence (provided by Earl Ruley, Massachusetts Institute of Technology); (3) a 3.3-kb HindIII/EcoRI lacZ fragment from the pSV-β-galactosidase vector (Promega Corp., Madison, Wis.); and (4) a 1.5-kb EcoRI insert of a human β-actin gene purified from the HFBCC49 plasmid (ATCC). Hybridizations were performed as described.

In vitro Cytotoxic Assay

Cells ($2 \times 10^3 /200$ µl) were seeded into individual wells of a 96-well microtiter plate (Microtest III, Becton-Dickinson, Linden Park, N.J.). Twelve hours later, cells were treated with ara-C for either 24 h or 96 h. The cells were fixed at varying intervals after ara-C exposure and stained with 200 µl of 0.05% methylene blue. The dye was eluted with 0.33 M HCl for 15 min with agitation. Absorbance was measured in a microplate reader (Model 3550, Bio-Rad) at 600 nm. Values were determined within the linear range and standardized to a control curve [Manome, Y. et al. Cancer Res. 54:5408–5413 (1994)].

Sensitivity of 9L-Neo cells to ara-C treated in the presence of 9L-dCK transfectants (bystander effect). Bystander effect was determined as previously described [Freeman, S. M. et al. Cancer Res. 53:5274–5283 (1993)]. Briefly, 9L-Neo cells were mixed with 9L-dCK cells at different ratios and then plated in 60-mm culture dishes at $1 \times 10^5$ cells/plate. Cells were then treated with 200 nM ara-C for 72 h, washed and counted using a Coulter counter model ZF (Coulter Electronics Inc., Hialeah, Fla). Bystander effect experiments to determine requirement for direct cell-to-cell contact were performed as previously described. Ibid. Briefly, $2.5 \times 10^4$ 9L-Neo cells were plated in the bottom chamber of transwell microliter plates. 9L-dCK cells ($4.5 \times 10^4$) were then either directly mixed with the 9L-Neo cells in the bottom chamber or plated in the upper chamber, which is separated from the bottom chamber by a 3.0 µm porous membrane. Ara-C (200 nM) was added the next day and cell viability was determined by dye exclusion method 5 days later. Statistical analysis was performed using an unpaired, two-tailed, Student's t-test.

Pharmacokinetic Studies of Stable Transfectants

Assay of ara-C incorporation into DNA. Cells in logarithmic growth phase were washed twice with PBS and incubated in serum-free medium with either $10^{-7}$ or $10^{-8}$ M [$^3$H]ara-C (25 Ci/moll, Moravek Biochemicals Inc., Brea, Calif.). Three and 6 h later, labeled cells were harvested, and digested by the addition of 2.5 mg proteinase-K (Boehringer-Mannheim, Indianapolis, Ind.) in 2 ml of 10 mM Tris (pH 7.4), 1 mM EDTA, and 0.5% SDS. Subsequent purification was accomplished by phenol extraction. The nucleic acids were precipitated, centrifuged, treated with RNase A and then assayed for radioactivity [Major, P. D., et al., Proc. Natl. Acad. Sci. USA 78:3235–3239 (1981)].

Determination of ara-CTP pools by HPLC. Ara-CTP pools were determined as previously described [Kufe, D., et al., Blood 64:54–58 (1984); Major, P. P., et al., Biochem. Pharmacol. 31:2937–2940 (1982)]. Briefly, cells were exposed to 10 µM [$^3$H]ara-C for 3 h, and then harvested and washed with PBS at 4° C. Nucleotides were precipitated by the addition of 12% perchloric acid ($HClO_4$) for 30 min on ice. The supernatant was neutralized with 1 M Tris-HCl (pH 10.0). The nucleotides in the acid-soluble fractions were analyzed on an HP1090 (Hewlett-Packard, Waldbronn, Germany) HPLC equipped with AX-10 anion-exchange column, using a linear gradient of 2.5 mM $KH_2PO_4$ (pH 3.0) to 0.5 M $KH_2PO_4$ (pH 4.4) over 30 min. The eluant fractions were collected, and radioactivity was measured by liquid scintillation counting.

Animal Studies

Implantation of intradermal tumors. One million 9L-Neo or 9L-dCK cells were injected intradermally into the right flank of Fischer 344 rats. Tumor volume was calculated by multiplying the values of three perpendicular diameters. Statistical analysis was performed using an unpaired, two-tailed, Student's t-test.

Implantation of intracerebral tumors. 9L-Neo and 9L-dCK cells were stereotaxically implanted into the right caudate nucleus of Fischer 344 rats using a modification of the method of Kobayashi [Kobayashi, N. et al. *J. Neurosurg.* 53:808–815 (1980)]. In brief, male Fischer 344 rats (150–175 g) were anesthetized and placed in a small animal stereotaxic frame (Kopf Instruments). Tumor cells ($2 \times 10^4$/ 10 μl) were injected with a 701 Hamilton syringe over 30 s to a depth of 4.5 mm, 1.3 mm posterior and 4 mm to the right of the bregma. This method resulted in a 100% yield of intracerebral tumors with relatively little leptomeningeal or intraventricular spread. Statistical significance of survival between different groups was assessed using log rank analysis of Kaplan Meier survival curves.

Treatment of animals. Ara-C was administered by subcutaneous injection at the dose of 200 mg/kg every 8 h for 2 days, followed by another 2-day course 6 days later. The dose of ara-C used in these studies was 200 mg/kg, a dose previously shown to be equivalent to high-dose ara-C (1 g/m$^2$) in humans [Colly, L. P. et al. *Med. Pediatr. Oncol.* 209 (suppl.1) 209–220 (1982); Colly, L. P. et al. *Cancer Res.* 46:3825–3827 (1986); Colly, L. P. et al. *Leuk. Res.* 8:945–952 (1984); Vaughan, W. P. et al. *Cancer Res.* 43:2005–2009 (1983)].

Recombinant Adenovirus

The dCK-cDNA was cloned into the NotI site of a shuttle plasmid, Ad. CMVβgal (kindly provided by Ronald Crystal). The resulting shuttle plasmid, pCMV-dCK, was cotransfected into 293 cells with the pjM17 plasmid containing the adenoviral type 5 genome (kindly provided by Frank Graham) as previously described [Graham F. L., et al., *J. Gen. Virol* 36:59–72 (1977); McGrory W. J., et al., *Virology* 163:614–617 (1988)]. Calcium phosphate precipitation method was used for DNA transection. Recombinant adenovirus was isolated from a single plaque, expanded in 293 cells, and purified by double cesium gradient ultracentrifugation as described [Graham F. L., et al. *Methods in Molecular Biology* (ed. Murray, E. J.) 109–128 (Humana Press, Inc., Clifton, N.J. 1991)]. The titer of purified adenovirus was determined in a spectrophotometer at 260 nm and by plaque assays.

REFERENCES

Anderson, N. F. *Science* 256, 808–813 (1992).
Mullen, C. A. et al. *Proc. Natl. Acad. Sci. USA* 89, 33–37 (1992).
Culver, K. W. et al. *Science* 256, 1550–1552 (1992).
Early, A. P. et al. *Cancer Res.* 42, 1587–1594 (1982).
Mikita, T. et al. *Biochemistry* 27, 4698–4705 (1988).
Plagemann, P. G. W. et al. *Cancer Res.* 38, 978–989 (1978).
Chottiner, E. G. et al. *Proc. Natl. Acad. Sci. USA* 88, 1531–1535 (1991).
Housey, G. M. et al. *Cell* 52, 343–354 (1988).
Manome, Y. et al. *Biochem. Pharmacol* 45, 1677–1684 (1993).

All references mentioned herein are hereby incorporated by reference.

It is evident that those skilled in the art given the benefit of the foregoing disclosure may make numerous other uses and modifications thereof and departures from the specific embodiments described herein without departing from the inventive concepts, and the present invention is to be limited solely by the scope and spirit of the appended claims.

TABLE 1

Incorporation of ara-C into DNA (pmol)

|  | 9L-WT | 9L-Neo | 9L-dCK |
| --- | --- | --- | --- |
| 3 hours |  |  |  |
| $10^{-8}$ M | 0.054 ± 0.001 | 0.067 ± 0.007 | 0.288 ± 0.080* |
| $10^{-7}$ M | 0.359 ± 0.061 | 0.502 ± 0.198 | 1.408 ± 0.112* |
| 6 hours |  |  |  |
| $10^{-8}$ M | 0.305 ± 0.094 | 0.403 ± 0.101 | 2.912 ± 0.624** |
| $10^{-7}$ M | 1.905 ± 0.652 | 1.926 ± 0.259 | 6.081 ± 1.887** |

One million cells were treated with [$^3$H]ara-C (0.5 mCi/ml) for 3 or 6 h. After cells were harvested, DNA was extracted by proteinase K digestion followed by RNase treatment. Radioactivity of ara-C incorporated into DNA was counted and converted to a picomolar (pM) unit. The results represent the means ± s.d. of three independent experiments.
*P < 0.002 compared with controls.
**P < 0.02 compared with controls.

TABLE 2

Nucleotide pools in cells (pmol)

|  | 9L-WT | 9L-Neo | 9L-dCK |
| --- | --- | --- | --- |
| ara-CMP | 0.213 ± 0.066 | 0.223 ± 0.086 | 0.866 ± 0.103* |
| ara-CDP | 0.237 ± 0.078 | 0.197 ± 0.066 | 0.868 ± 0.168* |
| ara-CTP | 2.473 ± 0.292 | 2.033 ± 0.619 | 5.340 ± 0.690* |

One million cells were exposed to $10^{-7}$ M of [$^3$H]ara-C for 3 h. Nucleotides were extracted with 12% perchloric acid and analyzed by HPLC using an AX-10 anion-exchange column. Radioactivity in each ara-CMP, ara-CDP or ara-CTP, was counted and converted to a picomolar (pM) unit. The results represent the means ± s.d. of four independent experiments.
*P < 0.002 compared with controls.

We claim:

1. A method for enhancing the effectiveness of a molecule that is capable of being phosphorylated by deoxycytidine kinase (dCK) which comprises directly transducing a target cell in vivo with an effective amount of a nucleic acid sequence encoding a dCK protein having phosphorylation activity operably linked to a promoter, wherein the target cell is in a solid tumor, and said effective amount is the amount necessary to express the dCK protein that will phosphorylate said molecule.

2. The method of claim 1 wherein said molecule that is capable of being phosphorylated by dCK is a pyrimidine or purine deoxynucleotide.

3. The method claim 1 wherein said molecule capable of being phosphorylated by dCK is selected from the group consisting of ara-C(1-β-D-arabinofuranosylcytosine), dFdC (2,2'-difluorodeoxy-cytidine), aza-CdR(5-aza-2'-deoxycytidine), cladribine (2-chloro-2'-deoxyadenosine), zalcitabine (2',3'-dideoxycitine) and fludarabine (9-β-D-arabinofuranosyl-2-fluoradenine).

4. The method of claim 3 wherein said molecule is ara-C.

5. The method of claim 1 wherein the target cell is a malignant cell.

6. The method of claim 1 wherein the tumor cell a cell in a tumor is selected from the group consisting of cells a brain tumor, a breast tumor, a kidney tumor, a lymph tumor and colon tumor.

7. The method of claim 1, wherein the tumor is a glioma.

8. The method of claim 6, wherein said molecule that is capable of being phosphorylated by dCK is a pyrimidine or purine deoxynucleotide.

9. The method of claim 6, wherein said molecule capable of being phosphorylated by dCK is selected from the group consisting of ara-C(1-β-D-arabinofuranosylcytosine), dFdC (2, 2'-difluorodeoxy-cytidine), aza-CdR (5-aza-2'-deoxycytidine), cladribine (2-chloro-2'-deoxyadenosine), zalcitabine (2', 3'-dideoxycitine) and fludarabine (9-β-D-arabinofuranosyl-2-fluoradenine).

10. The method of claim 9, wherein said molecule is ara-C.

11. The method of claim 7, wherein said molecules that is capable of being phosphorylated by dCK is a pyrimidine or purine deoxynucleotide.

12. The method of claim 7, wherein said molecule capable of being phosphorylated by dCK is selected from the group consisting of ara-C(1-β-D-arabinofuranosylcytosine), dFdC (2,2'-difluorodeoxy-cytidine), aza-CdR (5-aza-2'-deoxyctidine), cladribine (2-chloro-2'-deoxyadenosine), zalcitabine (2', 3'-dideoxycitine) and fludarabine (9-β-D-arabinofuranosyl-2-fluoradenine).

13. The method of claim 12, wherein said molecule is ara-C.

14. The method of claim 1, which is used on individuals having brain tumors.

15. The method of claim 1, wherein the target cell is transduced by a vector comprising the nucleic acid sequence encoding the dCK protein, said vector selected from the group consisting of a pox viral vector, a herpes viral vector, an adenovirus vector, and an adeno-associated virus vector.

16. The method of claim 1, wherein the target cell is transduced by an HIV-based virus vector.

17. The method of claim 7, wherein the target cell is transduced by a vector comprising the nucleic acid sequence encoding the dCK protein, said vector selected from the group consisting of an adenovirus vector, an adeno-associated virus vector, and a herpes virus vector.

18. The method of claim 17, wherein the vector is an adeno-associated virus vector.

* * * * *